US005759785A

United States Patent [19]

Tsai et al.

[11] Patent Number: 5,759,785
[45] Date of Patent: Jun. 2, 1998

[54] METHOD OF IDENTIFYING HORMONE ANTAGONISTS AND AGONISTS

[75] Inventors: Ming-Jer Tsai; Bert W. O'Malley; Sophia Yang Tsai; George Francis Allan, all of Houston, Tex.

[73] Assignee: Baylor College of Medicine, Houston, Tex.

[21] Appl. No.: 448,270

[22] Filed: May 23, 1995

Related U.S. Application Data

[63] Continuation of Ser. No. 166,800, Dec. 13, 1993, abandoned, which is a continuation of Ser. No. 946,727, Sep. 18, 1992, abandoned, which is a continuation-in-part of Ser. No. 882,772, May 14, 1992, abandoned.

[51] Int. Cl.[6] ........................ G01N 33/53; G01N 33/74
[52] U.S. Cl. ........................ 435/7.1; 435/23; 435/24; 436/501; 436/174; 436/175; 436/817
[58] Field of Search ........................ 435/6, 7.1, 7.2, 435/7.21, 23, 24; 436/501, 503, 536, 174, 175, 177, 178, 817

[56] References Cited

PUBLICATIONS

Ronald M. Evans, *The Steroid and Thyroid Hormone Receptor Superfamily*, 240 Science 889 (1988).

J.W.R. Schwabe and D. Rhodes, *Beyond zinc fingers: steroid hormone receptors have a novel structural motif for DNA recognition*, 16 Trends in Biochem. Sci. 291 (1991).

P.J. Fuller, *The steroid receptor superfamily: mechanisms of diversity*, 5 F.A.S.E.B. 2092 (1991).

V. Giguere et al., "Functional Domains of the Human Glucocorticoid Receptor", Cell, vol. 46, pp. 645–652, Aug. 29, 1986.

R. Heyman et al., "9–Cis Retinoic Acid Is a High Affinity Ligand for the Retinoid X Receptor", Cell, vol. 68, pp. 397–406, Jan. 24, 1992.

M. Bagchi et al., Ligand and DNA–dependent phosphorylation of human progesterone receptor in vitro, Proc. Natl. Acad. Sci. USA, vol. 89, pp. 2664–2668, Apr. 1992.

D. Picard et al., "A Movable and Regulable Inactivation Function within the Steroid Binding Domain of the Glucocorticoid Receptor", Cell, vol. 54, pp. 1073–1080, Sep. 23, 1988.

Iyengar et al J. Biol. Chem: 259 (1984) pp. 5222–5229.

Sabbah et al Proc. Natl. Acad. Sci. 88 (Jan. 1991) pp. 390–394.

Evans Science 240 (1988) pp. 889–895.

Friguet et al in *Protein Structure* ed Creighton IRL Press (1990) p. 309.

Cantor et al *Biophysical Chemistry: Techniques for the Study of Biological Structure & Function* W.H. Freeman & Co. (1980) pp. 443–448.

*Primary Examiner*—Lora M. Green
*Attorney, Agent, or Firm*—Fulbright & Jaworski L.L.P.

[57] ABSTRACT

The present invention provides a novel method of determining the antagonist and agonist activity of a compound for steroid hormone receptors. The present invention also provides a method of determining antagonist activity of a compound for a hormone receptor by inducing the conformational change in the receptor. In addition, the present invention provides a novel method of determining the level of agonist activity of a compound for steroid hormone receptors.

6 Claims, 19 Drawing Sheets

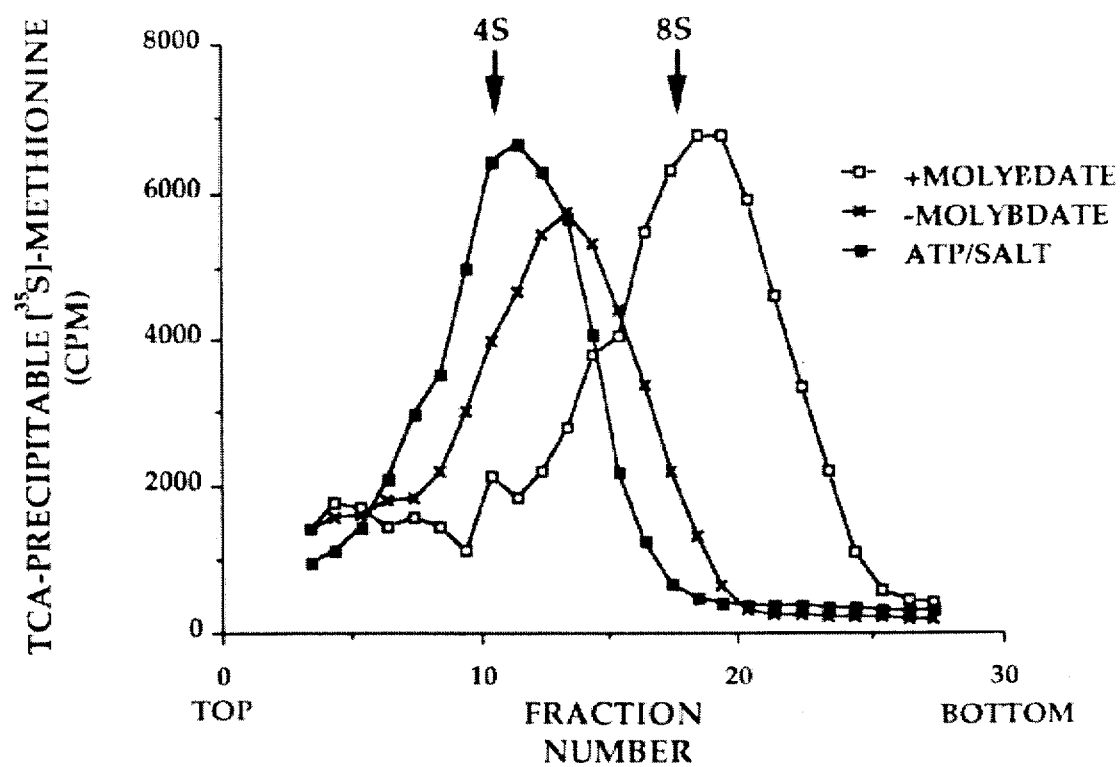

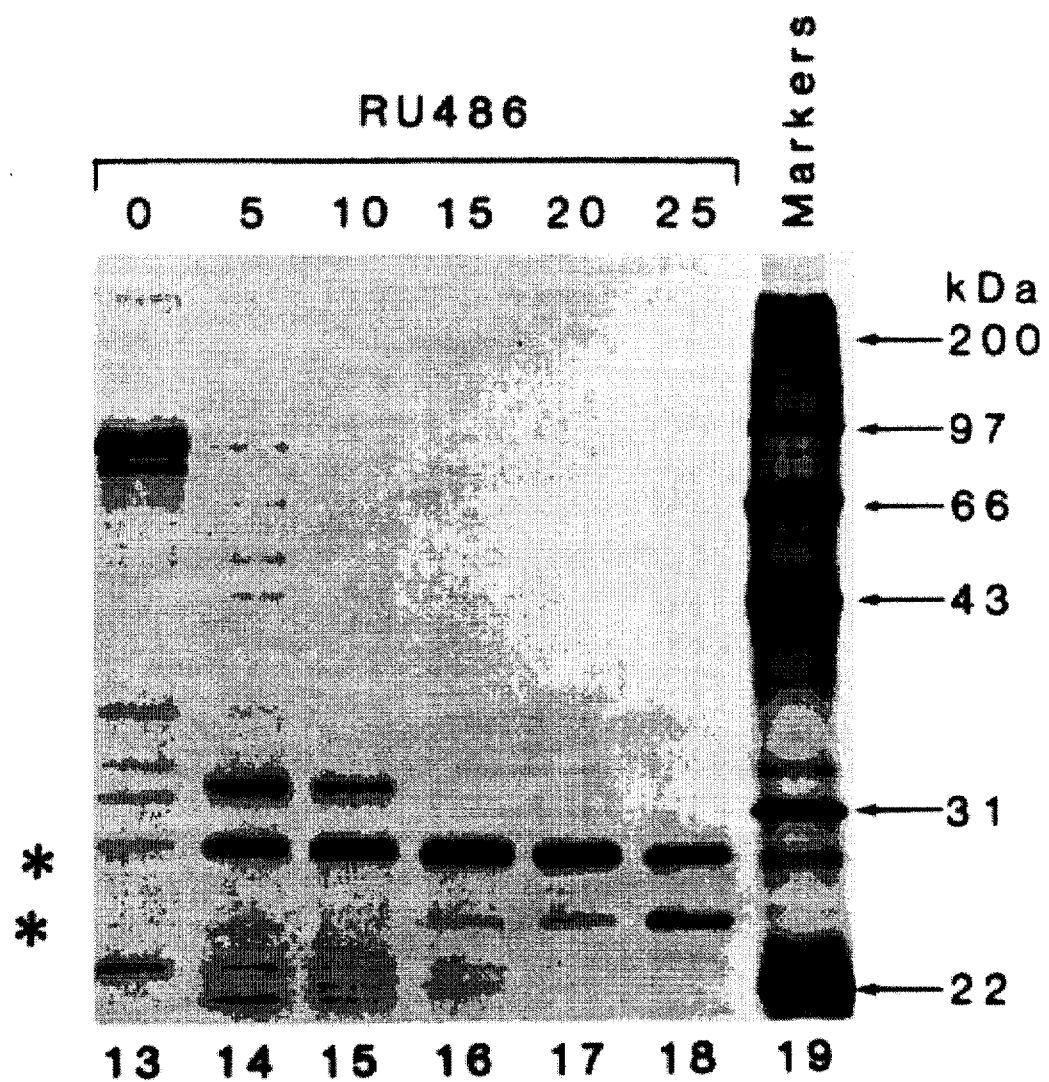
Figure 3A contd.

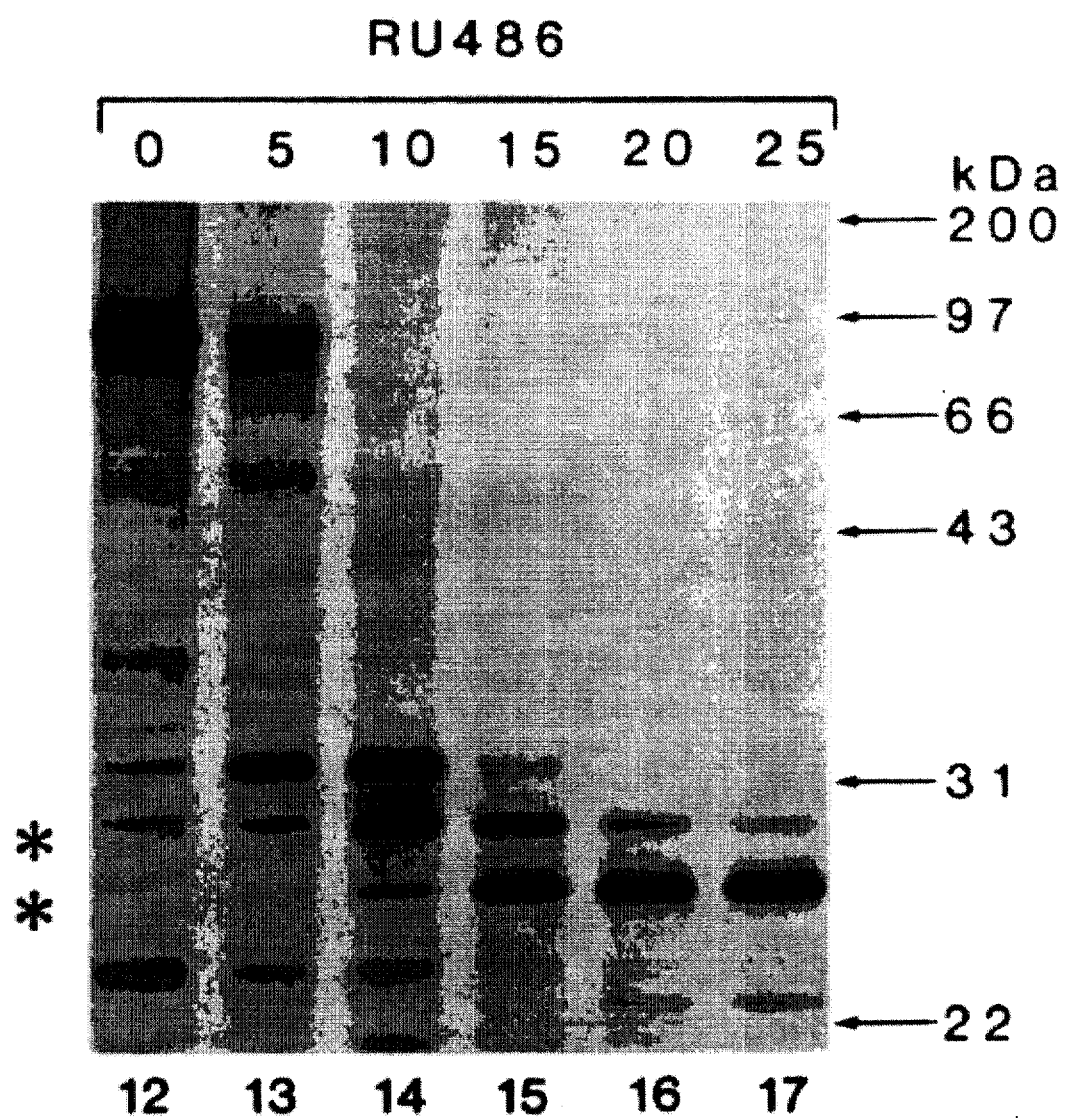
Figure 3B contd.

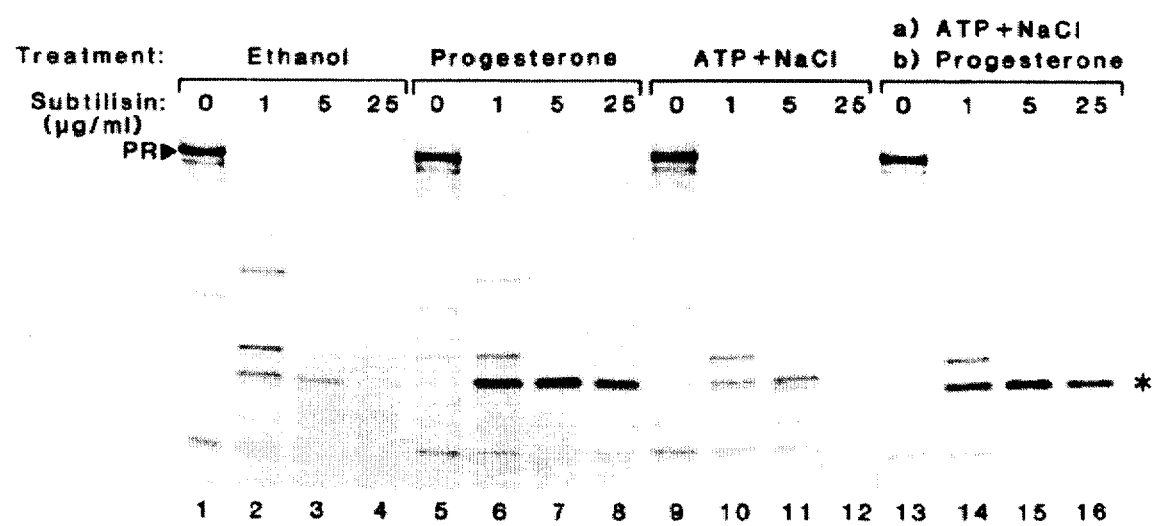

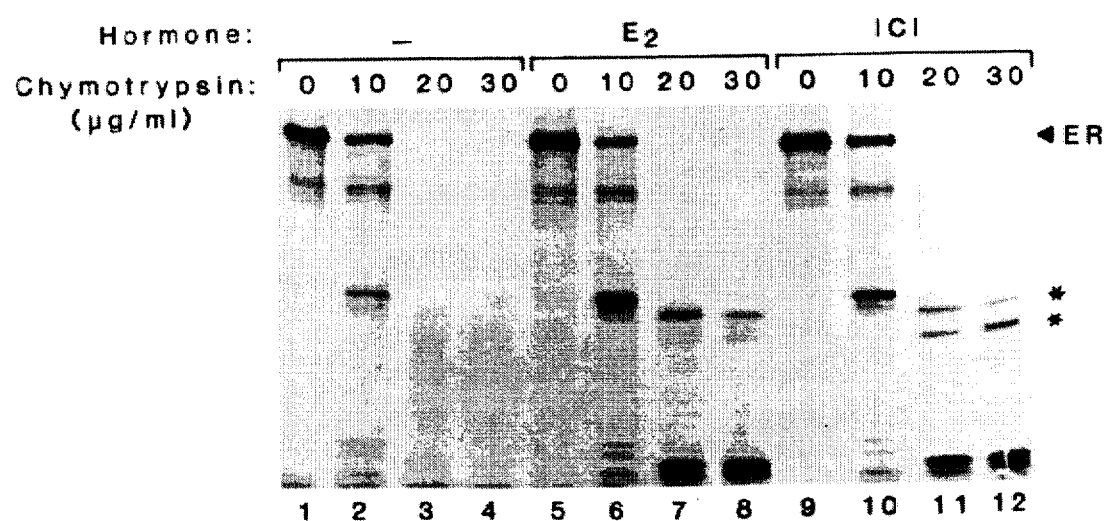

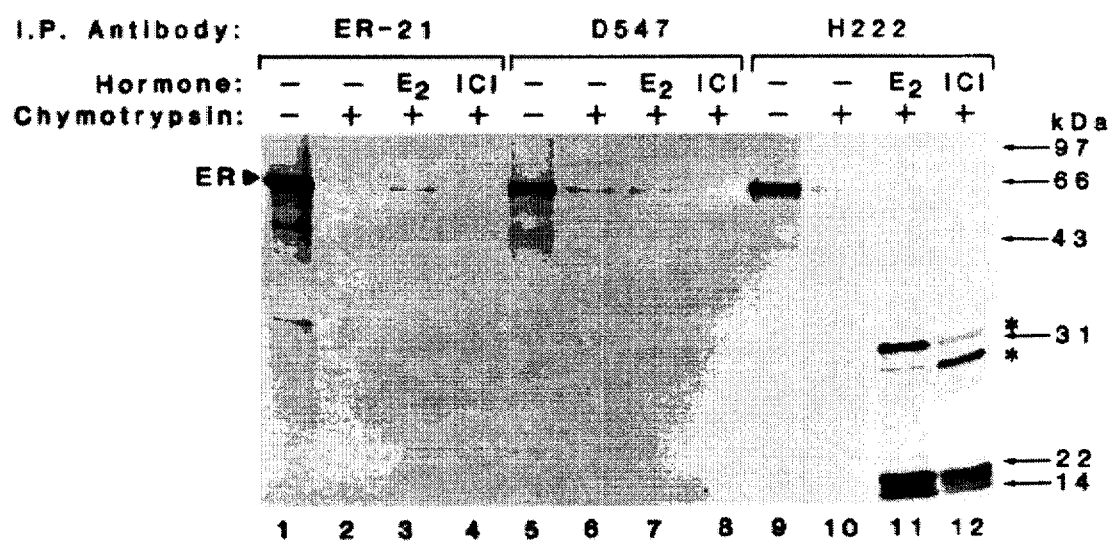

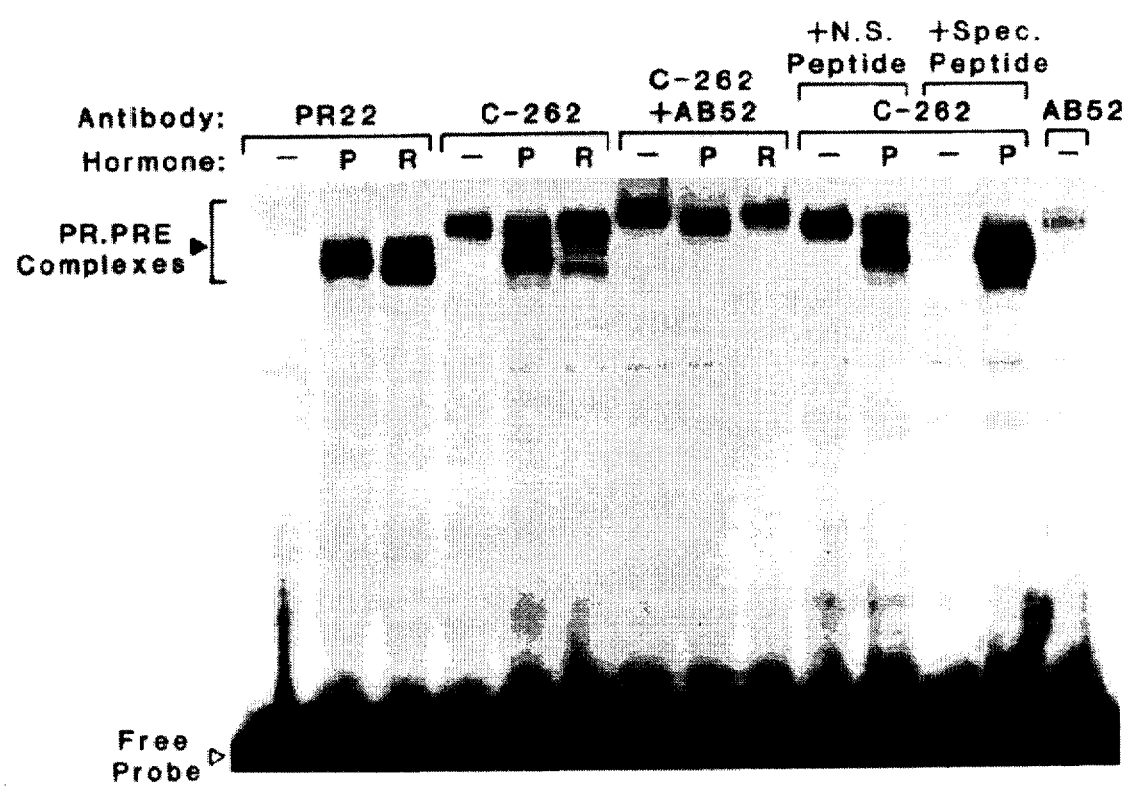

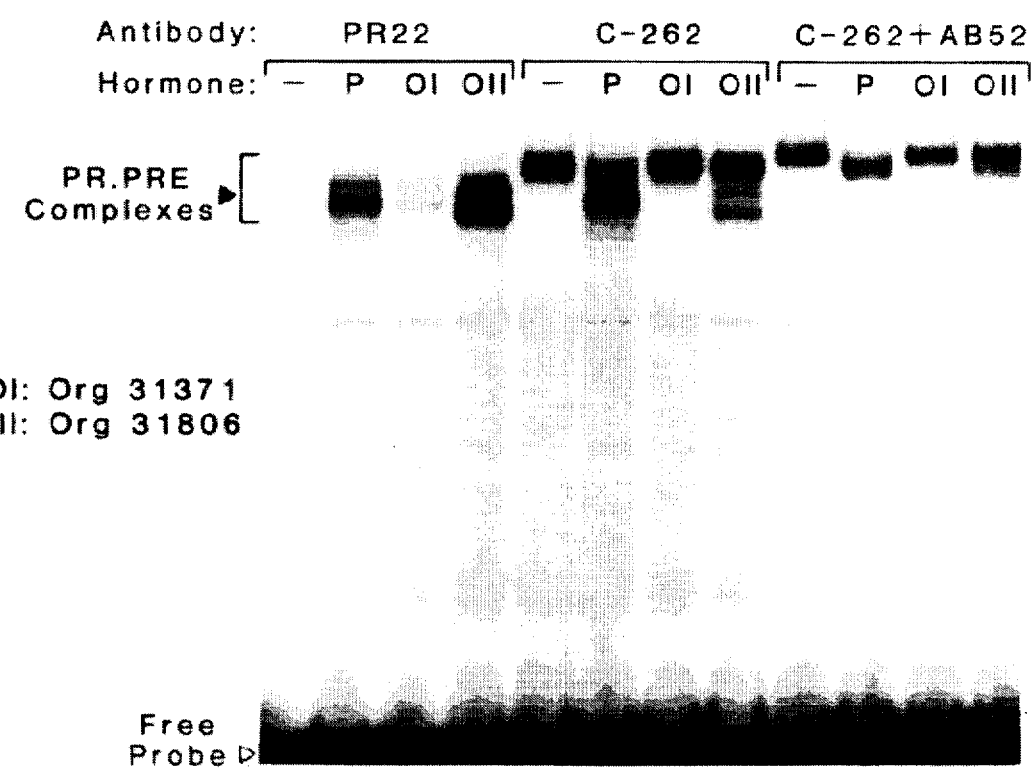

METHOD OF IDENTIFYING HORMONE ANTAGONISTS AND AGONISTS

CROSS-REFERENCE TO RELATED APPLICATION

This application is a continuation, of application Ser. No. 08/166,800 filed Dec. 12, 1993, which is a continuation of 07/946,727 filed Sep. 18, 1992, which is a continuation-in-part of 07/882,772 filed May 14, 1992, all of which are abandoned.

This invention was partially supported by grants from the United States Government. The government has certain rights in the invention.

BACKGROUND OF THE INVENTION

1. Field of the Invention

The present invention relates generally to the fields of molecular endocrinology and the receptor pharmacology. More specifically, the present invention relates to a novel method of determining the antagonist activity of a compound for steroid hormone receptors.

2. Description of the Related Art

Intracellular receptors mediate the effects of steroid hormones on gene expression and cell metabolism. The receptors comprise a family of structurally related polypeptides made up of discrete domains involved in DNA binding, ligand binding and transcriptional activation. Prior to recognition by the ligand, most steroid receptors are present within the cell in an inert, non-DNA bound form. Ligand binding transforms this receptor to a form which can recognize specific response elements adjacent to target genes, thereby modulating transcriptional activity by controlling the rate of initiation at the target promotor.

Several steroid receptors, including the progesterone receptor (PR) and the estrogen receptor (ER), sediment as large complexes of 8 to 10S on sucrose gradients, prior to ligand-mediated transformation. In addition to the receptor, these complexes contain a variety of heat shock proteins (hsp's). These proteins may inhibit receptor activity, and their dissociation following ligand binding may be sufficient for activation to the DNA binding form. However, the T47D cell-derived PR, in the transformed (4S) state, absolutely requires hormone for cell-free DNA binding and gene activation. Furthermore, this receptor can be purified free of all hsp's known to be associated with the 8S complex, yet still exhibits ligand-dependent activity. Thus, other events, separate from hsp removal, are necessary for receptor activation.

One candidate for activation is a phosphorylation step. Steroid hormone receptors, including PR and ER, are phosphoproteins. Following hormone administration in vivo or in vitro, PR becomes hyperphosphorylated as assessed by $^{32}P$ incorporation and by decreased mobility ("upshift") of the polypeptide on denaturing gels. Treatment of cultured mammalian cells with phosphatase inhibitors or kinase activators results in hormone-independent activation of progesterone response element (PRE)-containing reporters by co-transfected PR. However, human PR over-expressed in a baculovirus system does not exhibit phosphorylation-induced upshifting following progesterone treatment, but still binds with high affinity to specific DNA. Furthermore, hormone-dependent phosphorylation of isolated T47D PR occurs under cell-free transcription conditions only in the presence of PRE-containing DNA and a nuclear extract from HeLa cells, yet this receptor does not require the HeLa extract for binding to the PREs. Consequently, these combined data suggest that progesterone-induced phosphorylation is not necessary for DNA binding, but may be required subsequently.

Relevant to the mechanism of hormone activation is the mechanism of action of antihormones. Antihormones, typified by the antiprogestin Ru38486 and the antiestrogen ICI 164,384, are potent antagonists of hormone action in vivo. However, Ru38486 transforms 8S PR and facilitates DNA binding in vitro and in vivo in a manner similar to that of the agonist. One possible mechanism how the antihormone produces a transcriptionally inactive receptor is that antagonist-receptor complexes are structurally different from agonist-receptor complexes. Ru38486-bound receptor has anomalous sedimentation properties on sucrose gradients and, as a DNA-protein complex, migrates slightly faster than hormone-bound PR on nondenaturing gels.

Clearly, a long felt need and desire would be met by the development of methods for the determination of a compound's activity as a steroid hormone receptor antagonist or agonist.

SUMMARY OF THE INVENTION

The present invention provides a method of determining the degree to which a compound possesses antagonist activity for a steroid hormone receptor. This method comprises contacting a compound with a hormone receptor in vitro under conditions which allow the compound to bind to the receptor. A conformational change is then induced in the receptor and the receptor is measured.

In another embodiment of the present invention, there is provided a method of determining the agonist activity of a compound for a steroid hormone receptor. This method comprises combining the compound of interest with the steroid hormone receptor protein in vitro so as to induce a conformational change in the receptor protein. Subsequently, the conformational change and the receptor protein is detected by a variety of methods.

In yet another embodiment of the present invention, there is provided a method of distinguishing whether a drug is an antagonist of a steroid hormone receptor. The method comprises first deleting carboxy terminal amino acids from a steroid hormone receptor protein. Subsequently, the binding of the receptor protein to DNA is analyzed in the presence of the compound of interest.

BRIEF DESCRIPTION OF THE DRAWINGS

FIGS. 1(A) and 1(B) depicts the DNA binding and sedimentation properties of the in vitro translated progesterone receptor. In panel (A) Translated PR was incubated with 1 nM (lane 4), 10 nM (lane 3) or 100 nM progesterone (Prog., lanes 2 and 7–10), 100 nM Ru38486 (RU, lane 5) or 17β-estradiol (E$_2$, lane 6), or with an equal concentration (0.01% v/v)) of ethanol (lane 1). To the indicated samples, before the addition of probe, a 100-fold molar excess of unlabeled PRE (lane 7) or estrogen response element (ERE, lane 8;) oligonucleotides, or 1 μg each of anti-chick PR (lane 9) or anti-human PR (lane 10) monoclonal antibodies were added. Specific DNA binding was analyzed by EMSA. The second faster-migrating DNA-protein complex does not contain receptor (compare lanes 1 and 10). Translated PR was treated with either 100 nM R5020 (+hormone), in the presence (+molybdate) or absence (−molybdate) of 20 mM sodium molybdate, or 0.4M sodium chloride (salt) and 10 mM ATP. Samples were analyzed by sucrose gradient ultracentrifugation. The positions of peaks from parallel [$^3H$] R5020-labeled, molybdate-stabilized (8S) or salt-treated (4S) chick cytosol gradients are marked by arrows.

In FIG. 3, panel (C) samples were treated with 100 nM Org 31376 (lanes 508), Org 31806 (lanes 9–12), or an equal amount of ethanol (lanes 1–4).

FIGS. 4(A) and 4(B) show that progesterone induces a conformational change in the receptor independently of heat shock proteins. Panel (A) translated PR was incubated at room temperature for two consecutive 30 minute periods of time. For the first period, ATP and sodium chloride (NaCl) were added to 10 mM and 0.4M, respectively, to lanes 9–16. An equal volume of water was added to lanes 1–8. For the second period, progesterone was added to 100 nM (lanes 5–8 and 13–16) or ethanol to 0.01% (v/v) (lanes 1–4 and 9–12) with volumes being maintained equal. Aliquots were digested with subtilisin and analyzed as before. In FIG. 4, panel B receptors were treated with R5020 (lanes 5–12) or ethanol (lanes 1–4), in the presence (lanes 1–8) or absence (lanes 9–12) of sodium molybdate followed by subtilisin digestion.

FIGS. 6(A)–6(D) depict the specific conformational changes produced by estradiol and ICI 164,384 and Nafoxidine. In panel A translated ER was treated with 100 nM 17β-estradiol (E₂, lane 2) or ICI 164,384 (ICI, lane 3), or with ethanol (-,lane 1), and analyzed for binding to an ERE by EMSA. In FIG. 6, panel B, ER-containing translation mixes were incubated with estradiol (lanes 5–8), ICI 164, 384 (lanes 9–12) or ethanol (-, lanes 1–4), before limited digestion with chymotrypsin. In FIG. 6, panel C, translated ER was incubated in the presence (lanes 5–8) or absence (lanes 1–4) of nafoxidine (100 nM) before limited digestion with chymotrypsin. In FIG. 6, panel D, ER was treated with ethanol (-, lanes 1, 2, 5, 6, 9, and 10), estradiol (lanes 3, 7 and 11) or ICI 164,384 (lanes 4, 8 and 12) before incubation with 20 µg/ml chymotrypsin (lanes 2–4, 608 and 10–12) or water (lanes 1, 5, and 9). Samples were then immunoprecipitated with the indicated antibodies.

FIGS. 8(A) and 8(B) show no progesterone inhibition of hPR supershift by the C-262 antibody. In panel (A), T47D extracts were treated in vitro with 100 nM progesterone (P, lanes 2, 5, 8, 11 and 13), RU486 (R, lanes 3, 6 and 9) or with an equal amount (0.01% (v/v)) of ethanol carrier (-, lanes 1, 4, 7, 10, 12 and 14), followed by the addition of N-terminal-binding (AB52, lanes 7 to 9 and 14) or C-terminal-binding (C-262, lanes 4 to 13) anti-hPR monoclonal antibodies, or a control anti-cPR antibody (PR22, lanes 1 to 3). In lanes 10 to 13, C-262 antibody had been previously incubated with its specific epitope (Spec. Peptide, lanes 12 and 13) or with a nonspecific epitope (+N.S. Peptide, lanes 10 and 11) before addition to the treated extract. Binding to a PRE was assessed by bandshift analysis. The positions of specific DNA-protein complexes and of free probe are indicated. (B) The effect of ligands on C-262 supershifting was tested as in (A), except that extracts were treated with 100 nM Org31376 (OI, lanes 3, 7 and 11), Org31806 (OII, lanes 4, 8 and 12) or progesterone (P, lanes 2, 6 and 10).

DETAILED DESCRIPTION OF THE INVENTION

DEFINITIONS

Figure 1A:
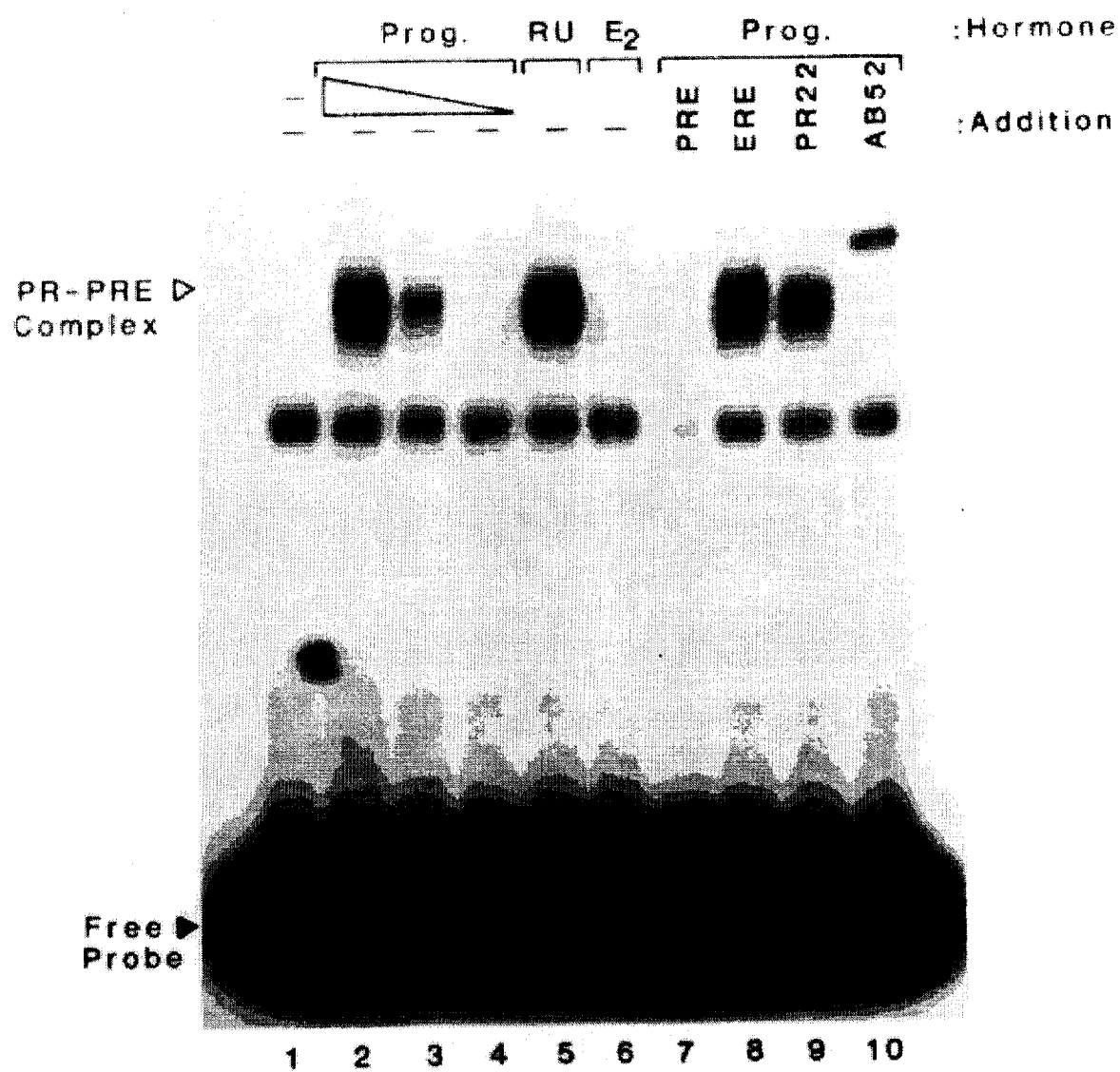

"Steroid Receptor Superfamily"-A grouping of over 20 structurally and functionally similar proteins (the "steroid receptor") as one large family. Examples of proteins in the steroid receptor superfamily include estrogen, glucocorticoid, mineralocorticoid, androgen, thyroid hormone, retinoic acid, retinoid X, vitamin D3 and testosterone.

"Orphan Receptor"-Members of the steroid receptor superfamily for which no ligands (hormone) have yet been identified.

"Hormone"-A small organic or protein compound (the former in the case of steroid hormone) which has effects on physiological metabolism and development. Hormones exert their effects within an individual cell by binding to and activating specific receptors.

"Antihormone"-Structurally similar to a hormone, an antihormone also binds to the receptor but causes its inactivation (rather than activation). Physiologically, antihormones reverse the normal (e.g., reproductive) or abnormal (e.g., breast tumor-causing) effects of their related hormones.

"Conformational change"-Proteins have a characteristic three-dimensional structure, or conformation, determined by the sequence of their building blocks (amino acids). Changes in this conformation will usually result in changes in the activity of the protein.

"Carboxy-terminal"-The downstream tail of a protein. As proteins are conventionally represented in linear form, the carboxy-terminal end is on the right.

"DNA binding domain or Hinge domain"-A "domain" is a segment of a protein which is structurally and/or functionally separate from the rest of the protein. Thus, the DNA binding domain is required for binding to DNA; the hinge domain has no specific function, but separates the DNA binding domain from the ligand binding domain.

"Accessibility of hinge region to proteolysis"-Proteolysis is the process of protein digestion (or degradation) carried out by proteolytic enzymes. These small proteins often recognize specific amino acids within the target protein for digestion, but only if they are accessible—i.e., available due to the folding of a protein characteristic of its structure. Thus, digestion of the hinge region is valuable because it lies between two large domains, acting as a "hinge."

"Immunodetection"-Detecting a protein or protein fragment using antibodies which specifically recognize it.

"Fluorescence detection"-A quantitative and qualitative means to detect a protein or protein fragment using fluorescent "tags".

"Radiodetection"-Detecting a molecular species (here, a protein fragment) using radioactive tracers. For example, in vitro translated protein fragments can be detected if some of their constituent amino acids are radioactively labeled. Radiation is easily detected by ongoing x-ray film to the radioactive source (autoradiography).

The present invention provides methods of determining agonist and antagonist activity of a compound for a steroid hormone receptor protein. To determine a steroid hormone antagonist, a compound of interest is combined with the steroid hormone receptor in vitro so as to induce a conformational change in the receptor. Subsequently, the conformational change in the receptor is detected. To determine the agonist activity of a compound, the compound is combined with the steroid hormone receptor protein in vitro so as to induce a confirmational change in the receptor. Subsequently, the confirmational change in the receptor protein is detected.

Generally, any hormone receptor protein in the steroid hormone superfamily is suitable for use in the methods of the present invention. Such hormone receptor proteins include those for estrogen, glucocorticoid, mineralocorticoid, androgen, thyroid hormone, retinoic acid, retinoid X, vitamin D3 and testosterone.

In determining a compound's antagonist activity for a steroid hormone receptor, the conformational change may be detected by digesting the steroid receptor protein with a proteolytic enzyme. Generally, any proteolytic enzyme which allows for a conformational change in steroid hormone receptor protein is useful in the method of the present invention. Preferably, proteolytic enzymes useful in the present invention include trypsin, V8, chymotrypsin and subtilisin.

Alternatively the conformational change may be detected by using a monoclonal antibody. Generally, any monoclonal antibody which allows for detection of the confirmational change in the steroid hormone receptor protein is useful. Preferably, the monoclonal antibody is raised against the carboxy terminal domain of the receptor, i.e., the last seventy amino acids.

Another method to detect a conformational change is to measure changes in fluorescence. The amino acid, tryptophan, can emit light (fluorescence) when excited with light at a wavelength of 280 nm (Stryer, L. "Fluorescence Spectroscopy of Proteins, Science 162, 526–540 (1968)). The amount of fluorescence emission is dependent on the surrounding environment of the tryptophan, i.e. on the nature of the adjacent amino acids in the three-dimension of protein. Thus, a conformational change which changes the surrounding environment of the tryptophan will result in a change in the extent of fluorescence emission. In the event that tryptophan residues in the native receptor are not located in an environment affected by ligand binding, one or more tryptophans can be chemically or recombinantly added to the C-terminal region of the steroid hormone receptor. The conformation of the C-terminal region has been shown to change drastically during ligand binding. Thus mutated receptor can then be used to screen agonists and antagonists of steroid hormones by measuring fluorescence changes from the inserted tryptophans during ligand binding.

In addition, the present invention provides, in an additional embodiment, a method of determining the antagonist activity of a compound for a steroid hormone receptor protein. This method comprises initially deleting carboxy terminal amino acids from the receptor protein. Subsequently, the binding of the receptor protein to DNA is assessed in the presence of the subject compound.

EXAMPLE 1

Plasmid construction

The coding sequence of A-form progesterone receptor was subcloned between the NcoI and EcoRI sites of sites of pT7βSal/Stu (Norman et al., Cell 55:989, 1988). The cDNA was inserted in two fragments: a 5' polymerase chain reaction (PCR)-generated fragment with NcoI and EaeI ends, and a 3' restriction fragment with EaeI and EcoRI ends. The PCR-generated NcoI site provides the initiator AUG of the coding sequence. Adjacent to this site in pT7βSal/Stu is an efficient Kozak's translation initiator sequence (Kozak, Nucleic Acids, Res. 15:8125, 1987, provided by the 5' untranslated region of the human β-globin gene (Norman et al., 1988). The resulting receptor coding sequence contains a substitution of a glycine codon for the wild-type serine codon at position two. The recombinant was linearized with EcoRI for transcription.

EXAMPLE 2

Coupled in Vitro transcription and translation

Linearized plasmids were transcribed with T7 RNA polymerase according to manufacturer's instruction, except that capped RNA was generated by a 15 minute incubation in 0.5 mM cap analogue and 20 µM GTP. The concentration of GTP was then raised to 0.5 mM and incubation was continued for 60 minutes. Reactions were not treated with DNase before phenol extraction and ethanol precipitation. Translation of 0.7 µg of the resulting RNA was carried out as instructed by Promega, except that reactions were supplemented with 1 µM zinc chloride. Unlabeled receptor was generated by replacing [$^{35}$S]methionine with 1 mM "cold" methionine. 10 to 50 pmol of trichloroacetic acid-precipitable receptor were synthesized per ml of translation mix.

EXAMPLE 3

Electrophoretic mobility shift assay

EMSAs were carried out as previously described (Bagchi et al., Mol. Cell. Biol., 2:1221, 1988), except that 100 ng (PR) or 1 µg (ER) of Poly(dI-dC)(dI-dC) were used as competitor and 10 mM $MgCl_2$ was used when testing estrogen receptor. 4 µl of unlabeled translation mix were used per 10 µl reaction. Proteins were incubated with ligand at room temperature (PR) or 37° C. (ER) for 10 minutes, followed by the addition of DNA and further incubation for 10 minutes. For the experiment in FIG. 2, all incubations were carried out at 30° C. in the presence of 300 U/ml calf intestinal alkaline phosphatase. All mixing was done by gentle vortexing. DNA-protein complexes were resolved on 4% (w/v) gels.

EXAMPLE 4

Sucrose gradient sedimentation analysis

Sedimentation analysis on 0 to 25% (w/v) gradients, and treatment of chick cytosols for sedimentation, were carried out according to (Bagehi et al., Nature 345:547, 1990). 25 µl of labeled translation mix were treated for 30 minutes at room temperature and then diluted before loading to 0.2 ml with gradient buffer containing 0.5 mg/ml bovine serum albumin. Fractions of 0.25 ml were trichloroacetic acid-precipitated as instructed by Promega for the estimation of incorporated [$^{35}$S]methionine.

EXAMPLE 5

Limited proteolytic digestion of translated receptors

To 5 μl of hormone-treated (10 minutes at room temperature (PR) or 37° C. (ER)) labeled translation mix, 0.5 μl of protease (diluted in water) was added followed by incubation for 10 minutes. The rate of digestion is dependent on the concentration of enzyme used. ER translation mixes were made 10 mM in MgCl$_2$ before hormone addition. 0.5 μl was removed and mixed with 10 μl of denaturing loading dye, boiled for 5 minutes, and immediately loaded on 1.5 mm thick 0.1% (w/v) sodium dodecyl sulphate-12% (w/v) polyacrylamide gels. Denaturing gel electrophoresis was performed as described in Promega's translation handbook. Following electrophoresis, gels were treated with 30% (v/v) methanol/10% (v/v) acetic acid, then with EN$^3$HANCE, and were vacuum dried at 60° C. for 30 minutes, followed by 80° C. for 45 minutes. Autoradiography was performed overnight. Promega's rabbit reticulocyte lysates average a protein concentration of 130 mg/ml; 5 μg of protease per ml of translation mix is therefore roughly equivalent to 60 ng of protease per mg of protein.

EXAMPLE 6

Immunoprecipitation of translated receptors

For precipitation of PR, 100 μl of a 100% (v/v) suspension (approximately 20 mg) of Protein A Sepharose CL-4B were incubated at 4° C. for 1 hour each with, first of all, 30 μg of rabbit antimouse immunoglobulin G, then 10 μg of primary antibody. The resin was washed three times at 4° C. with 1 ml of suspension buffer (TEGN: 10 mM Tris HCl, pH 7.4, 1 mM EDTA, 0.1% (v/v) Nonidet P-40). Five μl of PR which had been hormone-treated and digested with 25 μg/ml trypsin as above were supplemented with 0.5 μl of protease inhibitors (soybean trypsin inhibitor and leupeptin together, at final concentrations of 400 μg/ml and 4 μg/ml, respectively) and placed on ice. Ten μl of a 100% (v/v) suspension of the treated resin were added, incubated for 1 hour and washed four times at 4° C. with 1 ml of TEGN. Thirty μl of denaturing loading dye were added and the supernatants were loaded on denaturing polyacrylamide gels after boiling. The same procedure was used when precipitating ER, except that 1 μg of primary antibody was added to samples digested with 20 μg/ml chymotrypsin, then incubated for 1 hour on ice, followed by the addition of protein A Sepharose precoupled to the secondary antibody and incubation for a further hour.

EXAMPLE 7

Cell-free synthesized PR functions hormone-dependently

In order to obtain a source of labeled protein for a proteolytic analysis of receptor conformation, the coding sequence of the A-form human PR was cloned downstream of a strong Kozak's sequence, and the resulting in vitro transcribed RNA was translated in rabbit reticulocyte lysates in the presence of [$^{35}$S] methionine. A polypeptide of approximately 85 kilodaltons (kd) was produced, corresponding to the size of the 769 amino acid receptor.

Hormone-dependent activity of the in vitro synthesized PR was measured, i.e., its ability to bind DNA specifically was examined by electrophoretic mobility shift assay (EMSA) (FIG. 1A). Unlabeled receptors were incubated with a $^{32}$P-end-labeled oligonucleotide equivalent to a PRE from the tyrosine aminotransferase gene upstream region. Specific DNA-protein complexes were obtained only in the presence of 100 nM (lane 2) or 10 nM progesterone (lane 3). Specificity was confirmed by competition with the same (PRE, lane 7) or unrelated (ERE, lane 8) unlabeled oligonucleotides, and by supershifting with a monoclonal antibody directed against the amino-terminus of human PR (AB52, lane 10), but not by an antibody directed against chick PR (PR 22, lane 9). Furthermore, activation of DNA binding was hormone-specific, since estradiol (E$_2$, lane 6) failed to induce a specific complex. The antiprogestin Ru38486 promoted binding to the PRE that was at least as strong as that induced by an equal concentration (100 nM) of progesterone (RU, lane 5). In control experiments, mock translations yielded no major labeled polypeptides on denaturing gels or hormone-induced DNA-protein complexes on nondenaturing gels.

Rabbit reticulocytes contain large amounts of hsp90, hsp70 and hsp56, and in vitro translated glucocorticoid receptor sediments as a 9S complex on sucrose gradients. To determine if the translated PR could be associated with hsp's in a heteromeric complex, its size was tested by sucrose gradient ultracentrifugation. The receptor was first treated with hormone in the presence or absence of sodium molybdate, which stabilizes the 8 to 10S form. Treatment was also carried out with salt and ATP under conditions which completely dissociate the larger complex. As expected (FIG. 1B), translated PR sedimented as an 8 to 10S form in the presence of hormone plus molybdate, and was dissociated to a smaller 4 to 6S form in the absence of the stabilizer. Salt plus ATP treatment produced a 4S form. The data of FIG. 1 show that in vitro synthesized PR has structural and functional properties indistinguishable from those of the native receptor.

EXAMPLE 8

DNA binding is independent of phosphorylation

Figure 2:
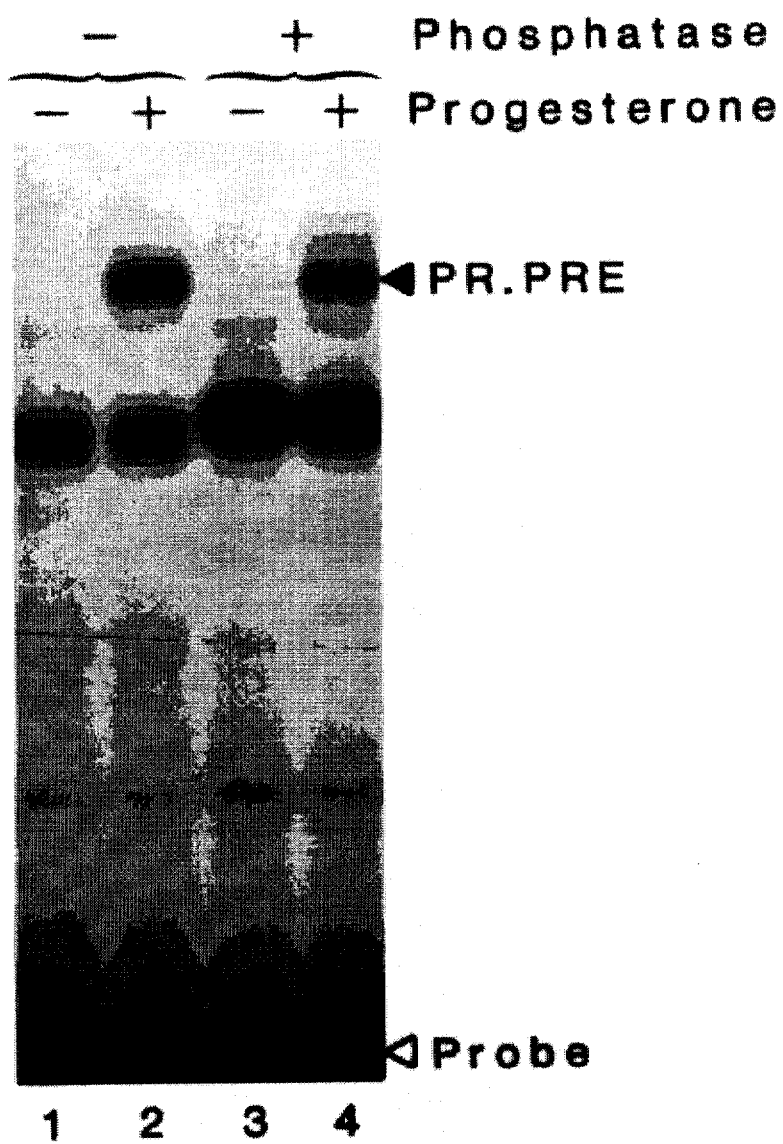
FIG. 2 shows the effect of phosphatase treatment on PRE binding. Translated PR was incubated with 100 nM progesterone (lanes 2 and 4) or 0.01% (v/v) ethanol (lanes 1 and 3) in the presence of alkaline phosphatase (lanes 3 and 4) or an equal volume of buffer (lanes 1 and 2). Samples were incubated with hormone and analyzed by EMSA.

With reference to FIG. 2, translated PR was incubated with 100 nM progesterone (lanes 2 and 4) or 0.01% (v/v) ethanol (lanes 1 and 3) in the presence of alkaline phosphatase (lanes 3 and 4) or an equal volume of buffer (lanes 1 and 2). Samples were incubated with hormone and analyzed by EMSA as described above. Hormonal activation of receptors could involve two mechanisms other than heat shock protein dissociation, phosphorylation and conformational changes. The former does not have a mandatory role in activation of PR to the DNA binding form. To address the role of phosphorylation with regard to ligand activation of translated PR, an EMSA was performed in the presence or absence of calf intestinal alkaline phosphatase (FIG. 2). Treatment with phosphatase under similar conditions completely reverses hormone-dependent upshifting on denaturing gels. The continuous presence of phosphatase has only a minor effect on PR-PRE complex formation in the presence of progesterone (compare lanes 2 and 4, FIG. 2). The enzyme has a major stimulatory effect on formation of a nonspecific complex on the same gel. Therefore, phosphorylation may not be a requirement for activation of human PR to the DNA-binding state.

EXAMPLE 9

Partial proteolytic analysis of hormone- and antihormone treated PR.

Figure 3A:
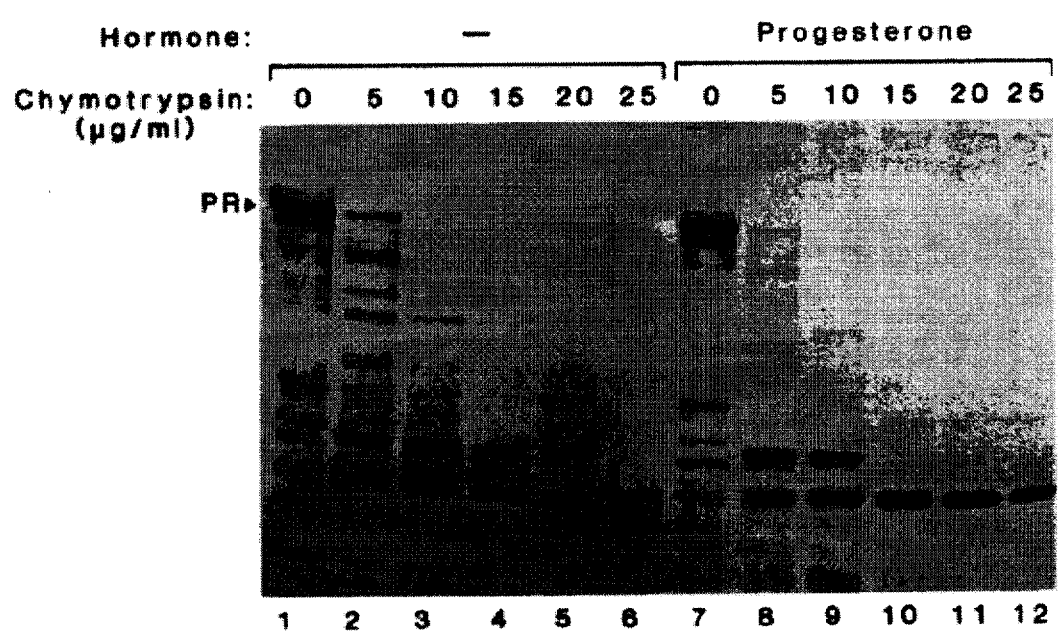
FIGS. 3(A)–3(C) illustrate the progesterone- and antiprogestin-specific conformational changes. Panel (A) receptors were incubated with 100 nM progesterone (lanes 7–12), Ru38486 (RU486, lanes 14–18) or 0.01% v/v ethanol (lanes 1–6) prior to digestion with the indicated levels of chymotrypsin. An equal amount of water was added for the undigested controls (lanes 1,7 and 13). Digestion products were analyzed by denaturing gel electrophoresis. The sizes of molecular mass markers (lane 19) are shown. Resistant fragments are indicated by asterisks. For the experiments in panels (A) and (B) of FIG. 3, and for those of FIGS. 4, panel A and 5, samples were separated on two parallel gels. In panel (B), digestion was with trypsin.
Figure 3B:
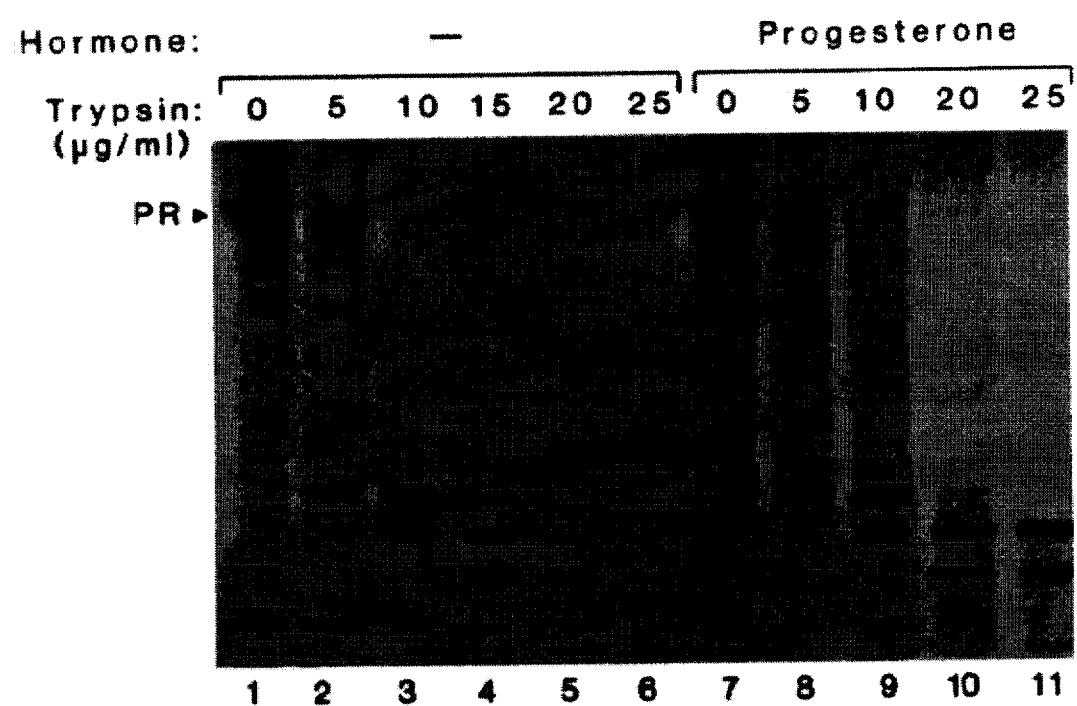

Proteolytic analysis is a powerful method for analyzing conformation changes within proteins. [$^{35}$S]methionine-labeled PR was treated with progesterone, Ru38486 or ethanol, then digested for a short period of time with different amounts of various proteases. Digestion products were analyzed by denaturing gel electrophoresis. Clearly distinct fragment patterns were observed for each treatment condition when digestion was carried out with chymotrypsin (FIG. 3A), trypsin (FIG. 3B) or subtilisin (FIG. 4). For all three proteases, the distinctions centered around one fragment. Relative to ethanol-treated receptor, a fragment of 30 kd was more resistant to digestion following progesterone treatment (compare lanes 6 and 12, FIG. 3A; lanes 6 and 11, FIG. 3B; lanes 4 and 8, FIG. 4A), while a 27 kd fragment was more resistant following antihormone treatment (compare lanes 6 and 18, FIG. 3A; lanes 6 and 17, FIG. 3B. Both fragments are extremely resistant to the proteases. The digestion is processive, therefore, it appears that the 27 kd fragment is derived from the 30 kd species, indicating that the structural changes induced by the two ligands involve the same general region of the intact receptor.

Figure 3C:
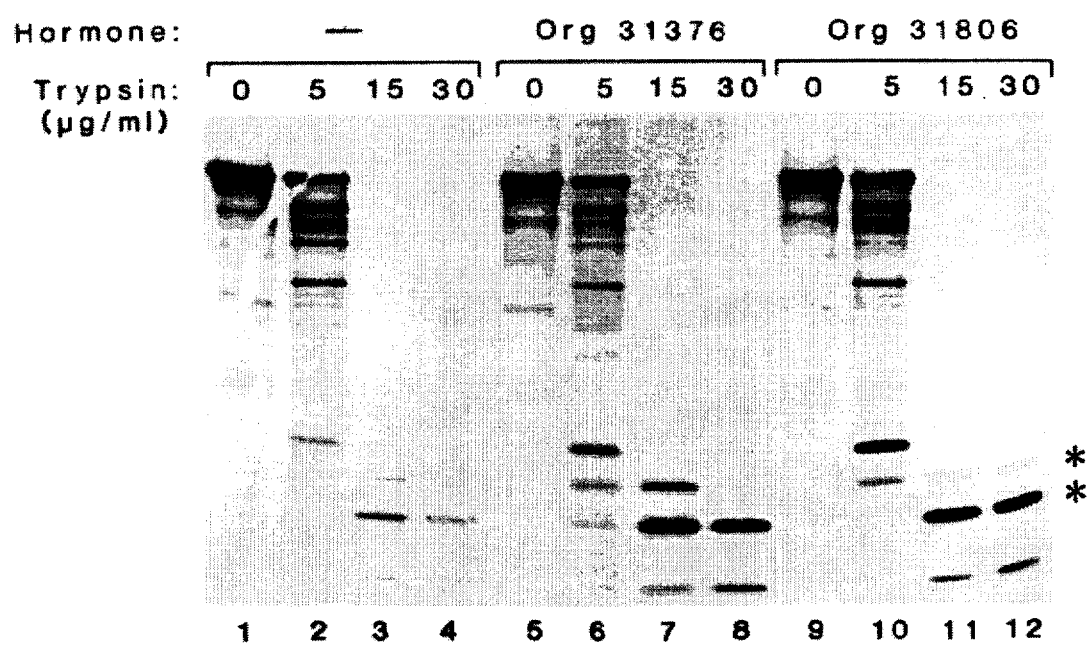

Two new antiprogestins, Org 31376 and Org 31806, strongly antagonize progesterone action in vivo and induce binding of translated PR to a PRE in vitro. Translated receptors were treated with these compounds and partially digested with trypsin (FIG. 3C). Both antihormones produce a proteolytic fragment pattern that is indistinguishable from that induced by Ru38486 (compare lanes 5–12, FIG. 3C with lanes 12–17, FIG. 3B). Thus, this pattern is indicative of a conformation characteristic to antagonist-bound PR.

EXAMPLE 10

The conformational change can be induced before and after hsp removal.

Prior to ligand binding, translated PR is present as an 8 to 10S complex in the reticulocyte lysate (FIG. 1B), presumably in association with hsp90, hsp70 and hsp56. One interpretation of the above results is that the change in protease accessibility observed after ligand binding is a consequence of dissociation of this heteromeric complex (FIG. 1B) rather than of direct effects on receptor structure. Arguing against this is the likelihood that the removal of associated proteins would decrease, rather than increase (as shown by FIG. 3), the resistance of receptor fragments to degradation. However, it remains possible that denuding the receptor has spontaneous destabilizing effects on conformation that are independent of ligand binding. To rule this out, two further experiments were performed.

First, translated PR was treated with ethanol, progesterone or salt plus ATP. Treated PR was analyzed for conformational changes by partial digestion with subtilisin (FIG. 4A). Although treatment with salt and ATP under the same conditions completely dissociates the 8S complex (FIG. 1B), and has been shown to remove all of hsp90 and the majority of hsp70 from the receptor, the resulting digestion pattern (lanes 10–12) was identical to that from undissociated, ethanol-treated PR (lanes 2–4). Furthermore, the "stripped" receptor could be digested to the hormone-specific pattern after subsequent incubation with progesterone (lanes 14–16). Salt plus ATP-treated translated PR did not bind specific DNA constitutively, but did upshift a PRE in the presence of hormone.

Figure 4B:
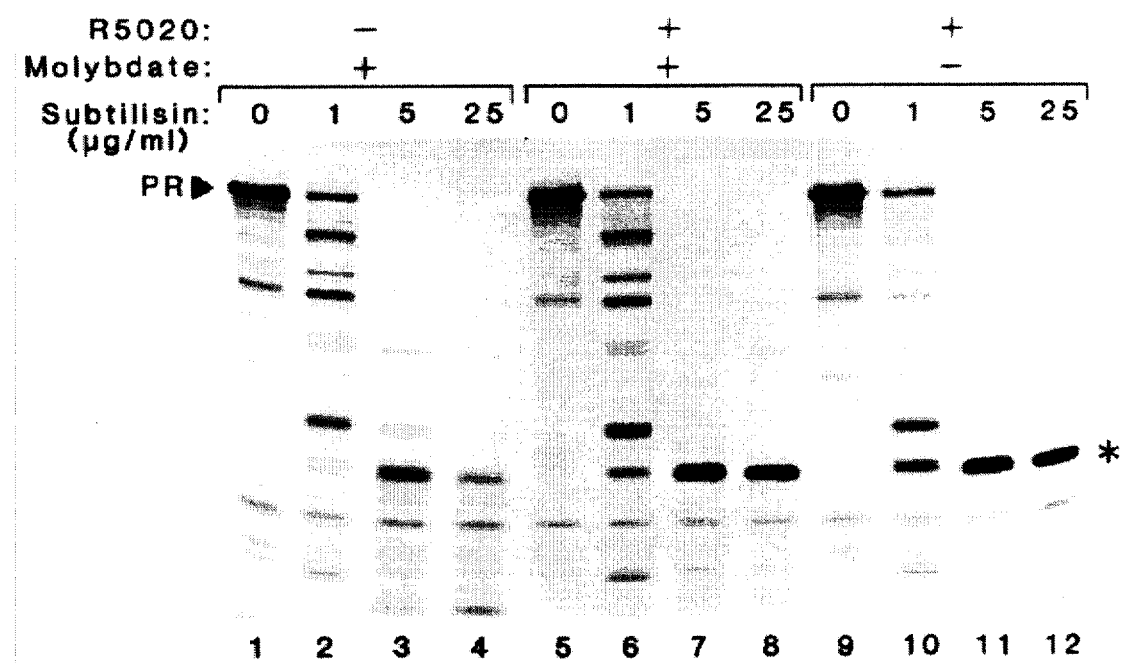

Secondly, PR was stabilized as an 8S complex by the addition of sodium molybdate prior to hormone. Protease digestion of molybdate-stabilized, R5020-bound (8S) receptor yielded a fragment pattern no different to that from non-stabilized (4S) receptor (FIG. 4B, compare lanes 5–8 with lanes 9–12). R5020 and progesterone induced the same conformational changes (compare lanes 5–8, FIG. 4A with lanes 9–12, FIG. 4B), and molybdate had no effect on the conformation by itself (compare lanes 1–4, Fib. 4A with lanes 1–4, FIG. 4B). Thus the observed structural change occurs independently of hsp's. That is, the structural change can be induced within the 8S complex while hsp's are still bound, and cannot be induced passively by removal of the hsp's by ligand-independent means. The structural effects require the presence of hormone, and are more than likely the consequence of direct modulation by the ligand.

EXAMPLE 11

The carboxy-terminus of the receptor undergoes ligand-induced conformational changes.

In the A-form of human PR, 69% of the methionine residues are located carboxy-terminal of the DNA binding domain. This fact, combined with the higher specific activity of the resistant fragments relative to the other fragments on denaturing gels (FIGS. 3 and 4), raised the possibility that the former contain all or part of the 30 kd ligand binding domain of the receptor. Immunoprecipitation of digested receptor was carried out using three antibodies, each directed against different parts of PR. The antibody AB52 is amino-terminal specific; antibody 1775 is derived from a rabbit polyclonal antiserum epitope-purified against a 15 amino acid region just amino-terminal of the DNA binding domain; and antibody C-262 is a mouse monoclonal antibody raised against the last 14 amino acids of the carboxy-terminal domain. Ligand-treated receptors were digested with a single concentration of trypsin and were either immunoprecipitated (FIG. 5, lanes 1–4 and 10–17) or loaded on a gel without precipitation (lanes 6–9). Digestion produced the expected resistant fragments from hormone(lane 8) or antihormone-treated PR (lane 9). Neither of these fragments were immunoprecipitated by AB52 (lanes 3 and 4) or 1775 (lanes 12 and 13), although both of these antibodies recognized the intact receptor (lanes 1 and 10). However, C-262 efficiently precipitated the 30 kd fragment (lane 16), but not the 27 kd fragment (lane 17).

The ligand binding domain of human PR is about 30 kd in size. Considering the position of the epitope recognized by C-262, the hormone-specific fragment may consist of the entire region downstream of the DNA binding or hinge domains. Potential cleavage sites for trypsin, chymotrypsin and subtilisin are grouped within the hinge region (which is a short stretch of amino acids immediately carboxy-terminal of the DNA binding domain), at positions appropriate for the generation of the 30 kd polypeptide. The antihormone-specific 27 kd fragment was not recognized by C-262. The 27 kd fragment is presumably different from C-262 by truncation of at least the carboxy-terminus. Over 20 additional potential cleavage sites for each of the proteases are evenly distributed downstream of the receptor's hinge region: all of these must be rendered less accessible to the enzyme by ligand binding.

EXAMPLE 12

Distinct ER conformations are induced by estrogen and antiestrogens.

Figure 6A:
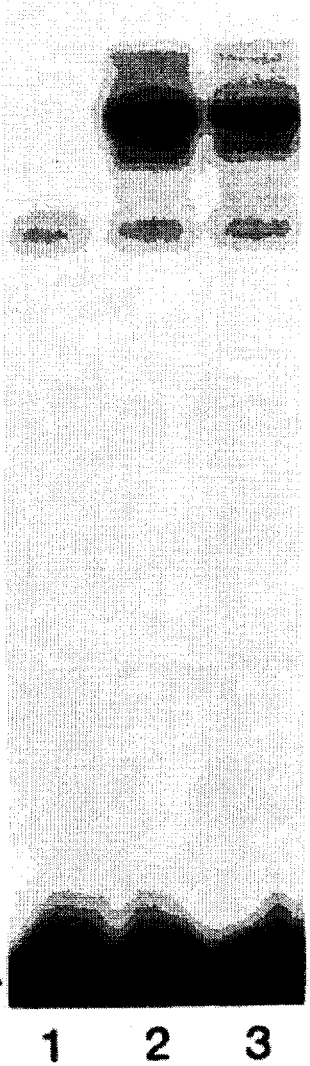
Figure 6C:
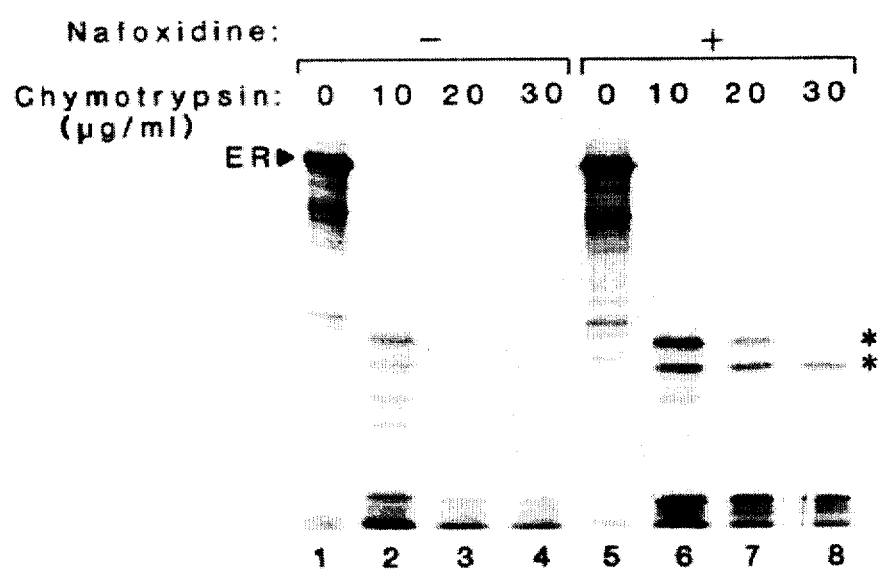

Human ER was synthesized in vitro producing a discrete 65 kd polypeptide (FIG. 6C, lane 1). This receptor binds in an estradiol-dependent manner to an ERE oligonucleotide derived from the vitellogenin A2 gene (FIG. 6A, compare lanes 1 and 2), but only at the magnesium concentration and incubation temperature described by Brown and Sharp, J. Biol. Chem., 165:11238, (1990). Constitutive ERE binding was observed. The antiestrogen ICI 164,384, a "pure" antagonist exhibits no detectable agonistic activity and nafoxidine also induces high affinity DNA binding (FIG. 6A, lane 3).

ER treated with estradiol, ICI 164,384, nafoxidine or ethanol under the same conditions (but in the absence of DNA) was subjected to limited proteolysis with chymotrypsin (FIG. 6B and 6C). Distinct fragment patterns were again observed for the hormone- and antihormone-treated receptors. All three ligands caused enhanced resistance of a series of peptides of 20 kd and smaller. In addition, estradiol induced a resistant fragment of approximately 32 kd (compare lanes 3 and 4 with lanes 7 and 8, FIG. 6B; see also FIG. 6D), while ICI 164,384 and nafoxidine enhanced the resistance of a 29 to 30 kd species which appears to be processed from the former (compare lanes 3 and 4 with lanes 11 and 12, FIG. 6B; compare lanes 3 and 4 with lanes 7 and 8, FIG. 6C).

This situation is remarkably similar to that seen with PR (FIG. 3). The size of the carboxy-terminal domain of ER downstream of the DNA binding and hinge domains (that is, the E+F domain) is 32 kd. Sixty-seven percent of the methionine residues of the receptor are located within this region. Thus, this resistant fragment may represent the ligand binding domain.

Immunoprecipitations were performed with specific ER antibodies: (1) ER-21, a rabbit polyclonal antibody purified against a peptide representing the first 21 amino acids of the receptor; (2) D547, a mouse monoclonal antibody recognizing a region adjacent to the carboxy-terminal side of the DNA binding domain; and (3) H222, a monoclonal which recognizes amino acids 463 to 528, the latter residue lying 67 amino acids from the carboxy-terminus. As can be seen in FIG. 6C, neither ER-21 nor D547 precipitated the 32 or 30 kd fragments (lanes 2–4 and 6–8), while both precipitated the full-length protein (lanes 1 and 5). H222, in contrast, recognized both proteolytic fragments, as well as the smaller degradation products (lanes 11 and 12). Thus, the resistant fragments induced after binding of hormone or antihormone to ER represent the entire ligand binding domain of the receptor (or fragments thereof), and the antihormone induces a conformation within this region different from that induced by the hormone. The observation of distinct conformational changes induced by antagonists thus extends to different steroid receptors.

EXAMPLE 13

Hormone-dependent conformational changes in retinoic acid receptor (RAR) and thyroxine receptor (TR)

Figure 7A:
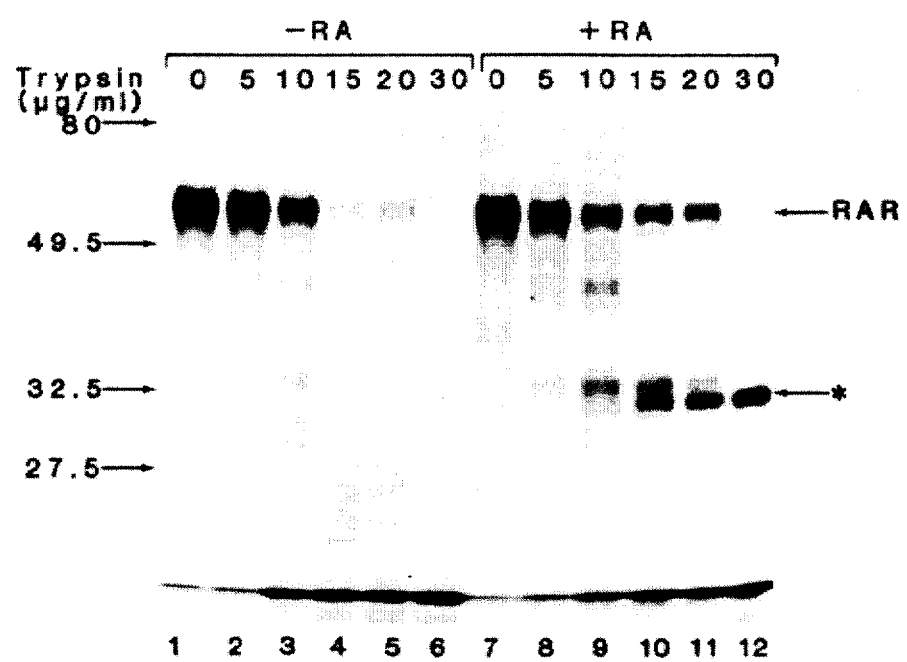
FIGS. 7(A) and 7(B) depict the specific conformation changes of retinoic acid receptor and thyroxine receptor produced by retinoic acid and thyroxine (T3) respectively. Translated RAR was treated with 2 µM retinoic acid (+RA, lanes 7–12) or ethanol (-RA, lanes 1–6) before limited digestion with trypsin. 7B translated TR was treated with thyroxine (+T₃, lanes 7–12 or ethanol (-T₃, lanes 1–6) before trypsin digestion.
Figure 7B:
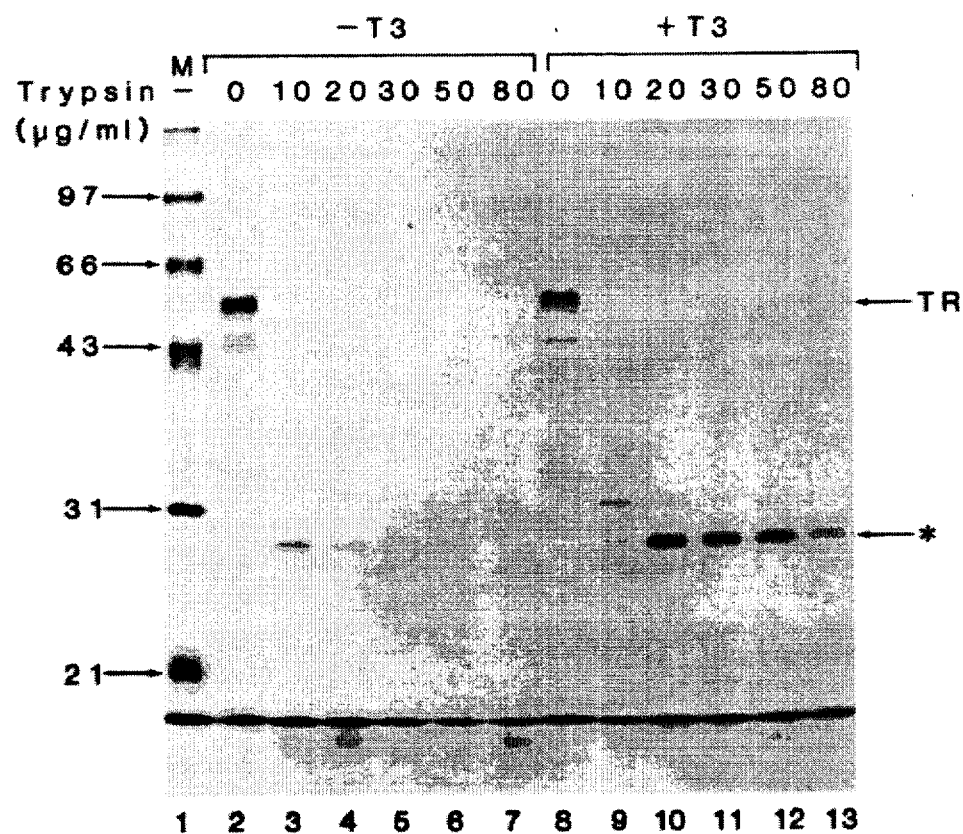

The receptors were translated as a polypeptides of predicted molecular weight (FIG. 7A and 7B, lane 1). Trypsin digestion of RAR and TR which had been preincubated with 2 µM retinoic acid and $10^{-7}$MT3 produced a resistant 31 kd fragment, which was not detectable following digestion of carrier-treated receptor (compare lanes 2–6 with lanes 8–12). The digestion pattern is remarkably similar to that arising from progesterone-treated PR. Since RAR, TR and PR have divergent biochemical properties and are conventionally classified in distinct receptor family subgroups, these data suggest that hormone-induced conformational changes are a general phenomenon occurring with the steroid receptor superfamily.

The C-terminal end of PR is not available for prelease digestion when bound to agonists. Thus, the C-terminal end of the receptor must be in a compact structure. If so, the C-terminal structure may not be available for antibody recognition as well. A monoclonal antibody (C-262), which was raised against the C-terminal 14 amino acids of PR was used to determine if there was a difference in the accessibility of the epitope when the receptor was bound to an agonist or an antagonist. As shown in FIG. 8A, addition of the C-262 antibody to the antihormone-bound receptor results in an upshift of the PR-DNA complex, suggesting that the C-terminal epitope is exposed to the solution after the receptor binds the antihormone (compare lanes 3 and 6, FIG. 8A). In contrast, prebinding of progesterone almost totally prevented recognition of the receptor by C-262 antibody (compare lanes 2 and 5), indicating that the epitope is masked when the hormone is bound to the receptor. Interestingly, C-262 itself was capable of inducing strong ligand-independent binding to the PRE (compare lanes 1 and 4). This result implies that binding to the C-terminal tail might be sufficient to elicit conformational changes leading to PRE recognition. Note, however, that AB52, which binds an epitope in the amino(N)-terminus of hPR, can also induce binding, albeit weakly (lane 14).

The epitope recognized by C-262 antibody was the C-terminus of the receptor. A peptide corresponding to the C-terminal 14 amino acid tail was preincubated with the antibody prior to addition to the band-shift reaction. Preincubation with this specific peptide abolished supershifting (compare lanes 4 and 5 with 12 and 13), while a nonspecific peptide had no effect (lanes 10 and 11). No upshifting was induced by the unrelated antibody PR22, which recognizes only chick PR (cPR, lanes 1 to 3). The complexes upshifted by C-262 contained hPR, since AB52 caused further supershifting (lanes 7 to 9). This experiment shows that RU486 and progesterone cause distinct receptor conformations such that the C-terminal epitope of C-262 is exposed when the receptor is free of hormone or when it is bound to RU486, but not when it is bound to progesterone.

Org31806 and Org31376 compounds were used in similar band shift experiments (compare FIG. 7A and B). Again, addition of the C-262 antibody resulted in supershifting of PR-DNA complexes when the receptor had been preincubated with the Org compounds (lanes 7 and 8) but not with progesterone (lane 6). The supershifted complexes contained PR, since AB52 recognized and further upshifted these complexes (lanes 9 to 12). No supershifting was seen when the nonspecific PR22 antibody was used (lanes 1 to 4). Taken together, these results demonstrate that antagonists cause a different conformational alteration of the receptor compared to agonists.

The present invention provides the first direct evidence for an active, rather than facilitative, role of ligand in receptor activation. Progesterone treatment of translated PR induces a dramatic conformational change within its structure. The conformational change is signalled by significantly enhanced resistance to proteolytic digestion of a 30 kd fragment (FIG. 3), and occurs in the absence of DNA in reticulocyte lysates. The conformational change can be induced while the receptor is stabilized in the 8S form (FIG. 4B), which argues that the effect of hormone binding on receptor conformation precedes, and thereby triggers, dissociation to the 4S complex. This is supported by the finding that hsp-free PR, which is both structurally indistinguishable from ethanol-treated receptor and functionally inactive without hormone, can be activated structurally (FIG. 4A) and functionally by the addition of progesterone. Similarly, estradiol treatment of translated ER induces a conformational change centered upon enhanced resistance of a 32 kd fragment (FIG. 6B).

The conformational change may be sufficient for induction of DNA binding. Translated PR forms a hormone-dependent complex with a PRE with the same efficiency in the presence or absence of excess phosphatase (FIG. 2). Moreover, hormone treatment of the translated receptor does not induce the upshifting on denaturing gels that is characteristic of steroid receptor phosphorylation (FIGS. 3 and 4). Thus, phosphorylation is not required either for the progesterone-induced conformational change or for DNA binding by PR.

The progesterone-induced 30 kd protease-resistant fragment is specifically immunoprecipitated by C-262 (FIG. 5) and must therefore correspond to the ligand binding domain. Likewise, immunoprecipitation analysis shows that the estrogen-induced 32 kd fragment represents the same domain in ER (FIG. 6C). However, the occurrence of additional conformational changes in other parts of the receptors cannot be ruled out.

FIG. 3 shows that RU38486-complexed PR is conformationally distinct from progesterone-bound PR. The conformation induced by the antagonist allows high affinity DNA binding (FIG. 1A), but presumably fails to present an activation surface appropriate for transcription. Two other novel antiprogestins, Org 31376 and Org 31806, produce a proteolytic fragment pattern that is indistinguishable from the Ru38486-induced pattern (FIG. 3C). Induction of the 27 kd fragment is thus a characteristic feature of progesterone antagonists. Similarly, the antiestrogens ICI 164,384 (FIG. 6B) and nafoxidine (FIG. 6D) enhance the resistance of an ER-derived proteolytic fragment which is again 2 to 3 kd smaller than that induced by the agonist. Thus, the structural change which follows antihormone binding may be similar in both receptors.

Figure 5:
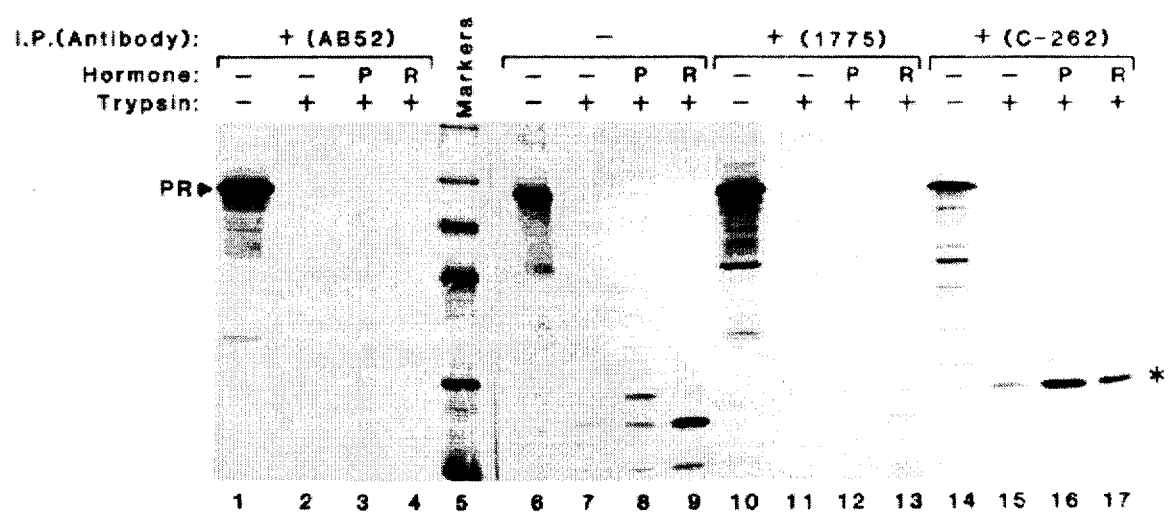
FIG. 5 illustrates that the conformational changes center on the ligand-binding domain. PR was treated as before with ethanol (-, lanes 1, 2, 6, 7, 10, 11, 14 and 15), progesterone (P, lanes 3, 8, 12 and 16) or Ru38486 (R, lanes 4, 9, 13 and 17), then digested with 25 µl/ml trypsin (lanes 2–4, 7–9, 11–13, and 15–17) or left undigested (lanes 1, 6, 10 and 14). Samples were either immunoprecipitated with the indicated antibodies (I.P.+, lanes 1–4 and 10–17) or left on ice in parallel (I.P.-, lanes 6–9), prior to gel electrophoresis.

As with the hormone, antihormones have a major effect on folding of the ligand binding domain. However, the antihormone-induced resistant fragment of PR is approximately 30 amino acids shorter than the hormone-specific fragment, and FIG. 5 shows that at least some of these amino acids have been removed from the carboxy-terminal end. The same may be true for ER and its antihormones (FIG. 6).

All patents and publications mentioned in this specification are indicative of the levels of those skilled in the art to which the invention pertains. All patents and publications are herein expressly incorporated by reference.

In conclusion, therefore, it is seen that the present invention and the embodiments disclosed herein are well adapted to carry out the objectives and obtain the ends set forth at the outset. Certain changes can be made in the method and apparatus without parting from the spirit and scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is therefore well adapted to carry out the objects and attain the ends and advantages mentioned, as well as others inherent therein.

What is claimed is:

1. A method of determining antagonist activity of a compound for a hormone receptor of the steroid hormone superfamily, comprising the steps of:

combining said compound with said hormone receptor in vitro so as to induce a conformational change in said receptor, and digesting said receptor with a proteolytic enzyme to detect said conformational change in said receptor, thereby measuring whether said compound is an antagonist of said receptor wherein the agonist-receptor fragment produced by the method is always greater than the antagonist receptor fragment.

2. The method of claim 1, wherein said hormone receptor is selected from the group consisting of estrogen, glucocorticoid, mineralocorticoid, androgen, thyroid hormone, retinoic acid, retinoid X, Vitamin D3, testosterone and orphan receptors.

3. The method of claim 1 wherein the proteolytic fragments of said receptor are separated by electrophoresis in a denaturing gel.

4. The method of claim 1, wherein said proteolytic enzymes are selected from the group consisting of trypsin, V8, chymotrypsin and subtilisin.

5. The method of claim 1, wherein said conformational change is in the carboxy terminus of the receptor.

6. The method of claim 1 wherein the agonist-receptor fragment is always 30 kDa or greater and the antagonist-receptor fragment is always less than 30 kDa.

* * * * *